United States Patent [19]
Raitto

[11] 4,178,941
[45] Dec. 18, 1979

[54] METHOD FOR DRAWING A BLOOD SAMPLE

[75] Inventor: Russell G. Raitto, Fitzwilliam, N.H.

[73] Assignee: Concord Laboratories, Inc., Keene, N.H.

[21] Appl. No.: 795,187

[22] Filed: May 9, 1977

Related U.S. Application Data

[60] Division of Ser. No. 715,678, Aug. 19, 1976, abandoned, which is a continuation of Ser. No. 542,578, Jan. 20, 1975, abandoned.

[51] Int. Cl.² ............................................. A61M 5/00
[52] U.S. Cl. ................................................ 128/763
[58] Field of Search ................ 128/2 F, 2 G, DIG. 5, 128/218 PA, 218 C

[56] References Cited

U.S. PATENT DOCUMENTS

| | | | |
|---|---|---|---|
| 3,753,432 | 8/1973 | Guerra | 128/2F |
| 3,930,492 | 1/1976 | Hatsuno et al. | 128/2 F |
| 4,041,934 | 8/1977 | Genese | 128/2 F |

*Primary Examiner*—William E. Kamm
*Attorney, Agent, or Firm*—Sewall P. Bronstein

[57] ABSTRACT

Improved method for taking blood or other fluid samples, particularly arterial samples for blood gas testing or the like, which comprises using a disposable syringe having a syringe body, a piston or plunger having a compressible end piece which forms a seal with the inner surface of the syringe body, and a means for preventing compression or deformation of the compressible end piece against the end wall of the syringe body.

6 Claims, 4 Drawing Figures

METHOD FOR DRAWING A BLOOD SAMPLE

This is a division of application Ser. No. 715,678 filed Aug. 19, 1976 and now abandoned, which is a continuation application of Ser. No. 542,578 filed Jan. 20, 1975 and now abandoned.

BACKGROUND OF THE INVENTION

This invention relates generally to hypodermic techniques for obtaining blood samples, more particularly to a hypodermic syringe assembly for drawing blood from a patient, especially a syringe useful for drawing samples from the patient's arteries for blood gas analysis or other testing.

Various apparatus and methods for taking blood samples from patients have been previously known. Such samples are normally taken by means of a syringe which includes a cylindrical tube having a piston therein which, when pulled by an operator creates a suction force drawing blood into the tube through a nozzle coupled to a hypodermic needle. Many of the tests are performed on blood which is obtained from the veins of the patient. However, an increasingly important method of determining the medical status of a patient is the obtaining of arterial blood samples, particularly for testing the blood for its content of various gases. Such samples are tested for the partial pressure of oxygen, the partial pressure of carbon dioxide, the pH of the blood, the electrolyte balance, and various other tests known in the art.

The syringes previously used in obtaining arterial blood samples have been glass syringes, in which the cylindrical body is made of glass and the piston is a ground glass rod which closely fits within the cylinder. Generally the technique for taking samples with such devices comprises as a first step the drawing of an anticoagulant solution, such as sodium heparin, into the syringe. This material also acts as a lubricant for the walls so that the glass piston may move relatively freely within the cylinder. The syringe is inverted and all air is expelled from the chamber and needle, along with the bulk of the anticoagulant solution, which is normally far in excess of the amount needed for the blood sample. It is extremely important that all air be expelled from the syringe, since one of the tests performed is the measurement of the amount of oxygen present in the blood, and even minute contamination with air will prevent accurate measurement of that amount. After suitable preparation of the patient, the hypodermic is inserted into the artery, and blood is either forced into the syringe by the pressure of the blood in the artery, or is drawn into the syringe by withdrawing the piston. One advantage of the glass syringes previously used is the ease with which the piston may be moved within the lubricated chamber. The glass piston is ground to very close tolerances, so that it is sufficiently close to the syringe wall to prevent leakage, but sufficiently far away to allow formation of a thin film of the anticoagulant. Even very low blood pressures are usually sufficient to enter the syringe and force the glass piston backwards without any aid from the person taking the sample. Upon entry into the syringe the blood mixes with whatever anticoagulant solution remained in the needle and tip of the syringe after the excess has been expelled.

The glass syringes previously used have suffered from a number of disadvantages. They are expensive, since the grinding requires close tolerances, in the order of 0.0007 inches clearance between the piston and the cylindrical syringe body. They are easily breakable, which is especially costly after the sample has been taken. The glass piston and the glass barrel of each syringe must commonly be matched during the grinding by the manufacturer, since variations in grinding from one piston to another may be sufficient to permit leakage of air or other material around the piston, which will contaminate the sample. Thus the cylinders and pistons cannot easily be individually mass produced, since the pistons often cannot be satisfactorily interchanged one with another in any given cylinder, as pointed out in U.S. Pat. No. 2,419,401 to Hinds. Further, because of the easy movement of the glass plunger in the cylinder, the plunger falls out of the cylinder of its own weight, and normally breaks on the floor, unless the syringe is carried needle end down. Special metal holders for the glass cylinder have been used to prevent this problem.

Attempts have been made to avoid these disadvantages by either manufacturing both the cylinder and the piston out of materials other than glass, such as plastics, or by using glass cylinders with plastic plungers or pistons. However, these attempts have not produced an acceptable product. In order to prevent leakage around the piston, these devices depend upon the use of a compressible tip on the end of the piston adjacent the hypodermic needle, which tip generally has a number of ribs which are larger than the inside diameter of the cylinder in their uncompressed state against the interior wall of the cylinder and form a seal. This type of seal, however, with the materials previously used, has made the movement of the piston within the cylinder more difficult, thus normally requiring manual withdrawal of the piston to obtain the blood sample. The handling of the syringe which is involved when manual withdrawal of the piston is required may cause traumatization of the artery from which the blood is being taken. A major problem has been the fact that when pressure is applied to expel the excess anticoagulant solution, the compressible tip on the end of the piston compresses and deforms against the end of the cylinder. When the piston is released prior to the insertion of the hypodermic needle into the artery, the pressure on the compressible tip is also released, which causes the piston to move back slightly, drawing a small amount of air into the tip of the hypodermic needle. Since the samples which are drawn to test for the amount of oxygen and carbon dioxide in the blood, are very small, e.g., 2, 5 or 10 ml, even minute amounts of oxygen leaked into the sample have potentially adverse affects on the results obtained. The compressibility of the plunger tip also causes nonuniformity in the amount of anticoagulant left in the tip of the syringe and hypodermic needle. As can be readily appreciated, the amount left will depend upon the amount of pressure used to expel the oxygen and excess anticoagulant, since greater pressure will compress or distort the compressible plunger tip to a greater degree, thus expelling more anticoagulant. If too little anticoagulant solution remains to be mixed with the blood, the blood may coagulate prior to testing and thus adversely affect the results obtained. If, on the other hand, too much anticoagulant solution is left in the syringe, its presence will also adversely affect the test, as is known in the art.

Accordingly, an object of the present invention is to provide a simple, inexpensive blood sampling syringe, particularly one suitable for taking arterial blood samples, which avoids the difficulties previously encountered with the glass syringes used for such purposes, and yet avoids any contamination of the sample which will interfere with the results obtained. It is a further object of the invention to provide such a syringe which is adapted to prevent air being sucked into the hypodermic needle when the plunger is released prior to taking the sample. It is a further object of the invention to provide such a syringe which is adapted so as to supply a uniform amount of anticoagulant solution to the blood sample being taken. It is a further object to provide such a syringe having an easily movable piston whereby the possibility of traumatization of the patient is minimized. It is a further object to provide a syringe having all of these advantages which is simple and inexpensive to manufacture, and thus of low cost to the patient, and extremely simple to operate in a manner which gives uniform and representative results.

Other objects and advantages of the present invention will be apparent from a reading of the present specification, or from the practice of the invention herein disclosed.

SUMMARY OF THE INVENTION

Briefly the above advantages are obtained in accordance with the present invention by providing a syringe in which the compressible end piece is prevented from contacting the end of the cylindrical body adjacent the hypodermic needle. This is preferably accomplished by providing a stoppage means on the piston which contacts the other end of the cylindrical syringe body at a point whereby the movement of the piston is stopped prior to contacting the end of the syringe. In this manner the compressible tip which forms a seal between the cylinder and the piston cannot be compressed against the end of the cylindrical chamber which bears the hypodermic needle and thus cannot force the piston to withdraw slightly upon being released from compression, and draw air into the tip of the needle. Similarly, the amount of anticoagulant solution supplied to the blood using the syringe of the present invention is very uniform from sample to sample, since the same amount is retained in the space left when the plunger or piston is fully inserted, no matter how much pressure is applied to the piston. Preferably, the compressible tip of the piston is also adapted to minimize friction between the piston and the inside of the cylindrical body, while maintaining an adequate seal.

The invention further comprises a method for drawing blood samples using the above described syringe. The method comprises expelling excess coagulant and any air that is present by moving the plunger into the syringe to the innermost limit, inserting the needle into a blood vessel of a patient and allowing the blood pressure of the patient to force the blood sample into the chamber and thereby move the plunger outwardly whereby the blood sample mixes with the anticoagulant left in the syringe. Additionally, preferably the blood sample fills the chamber and moves the plunger outwardly until an outer limit means stops further outward movement and determines the volume of the sample.

For a better understanding of the invention, reference is made to the following detailed descriptions to be read in conjunction with the accompanying drawing, in which FIG. 1 is a planar side view of the preferred syringe of the present invention;

Figure 1:
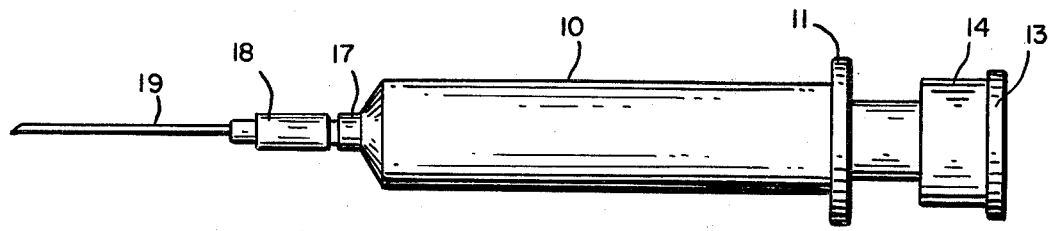
Figure 2:
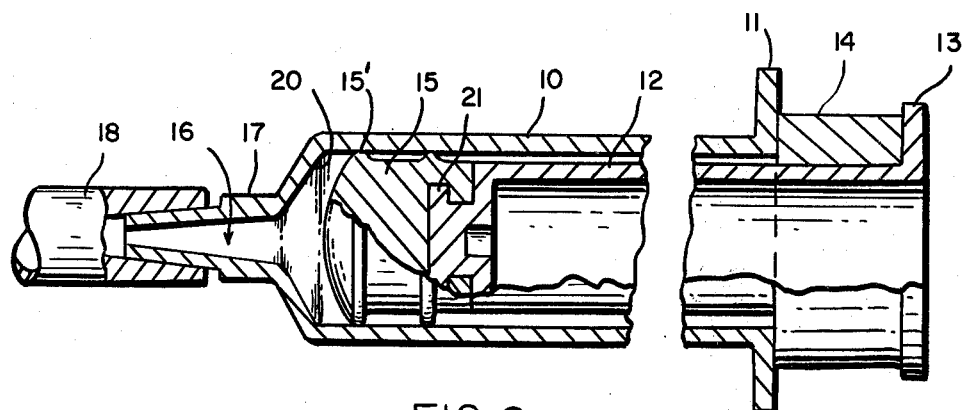
FIG. 2 is a longitudinal section of the syringe of FIG. 1.

Referring to FIGS. 1 and 2 of the drawing, the syringe depicted has a cylindrical body or tube 10, preferably made of an inexpensive substantially transparent plastic material, such as polyethylene or polypropylene, which is inert to, i.e. does not effect the sample to be taken, and which is substantially impermeable to oxygen and carbon dioxide. Other suitable materials, such as polystyrenes, acryllic or methacryllic polymers, and various glasses, are well known in the art. The cylindrical tube terminates at one end with finger piece 11. This piece is generally annular but can be any shape which provides support for two fingers, e.g. hexagonal, or taking the form of two tabs. The tube terminates at the other end in a tube wall 20 which bears an open tip 16 of reduced size. As shown, tip 16 is generally frustoconical, opening toward the cylindrical body 10. Tip 16 carries the hypodermic needle 19 through frictional engagement with cylindrical connecting member 18. As shown, tip 16 also bears an annular ring 17, which aids in the proper placement of the hypodermic needle on the syringe by limiting the distance up the tip to which connector 18 may be pushed.

The syringe also comprises a plunger or piston denoted generally at 12. At the outside end, this piston terminates in a thumb support surface shown as annular surface 13. The plunger terminates at the other end in a protrusion 21 which engages compressible end piece 15 having ridges 15' abutting the inside surface of cylindrical body 10.

Figures 3, 4:
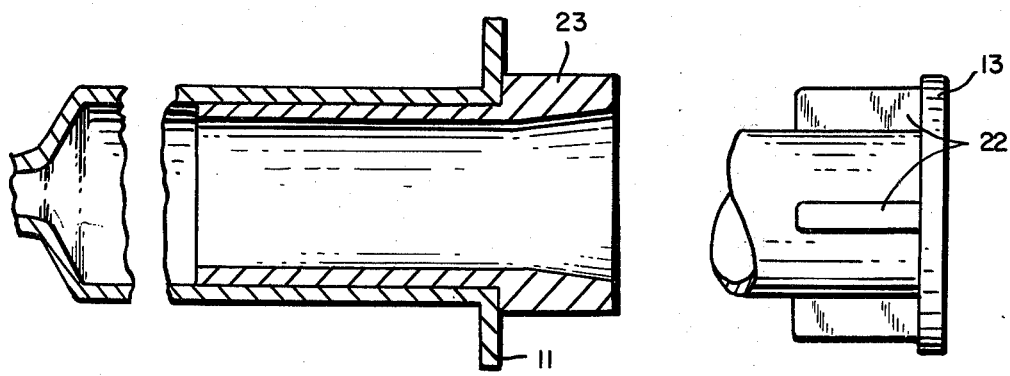
FIG. 3 shows an alternative embodiment of means for stopping the motion of the piston.
FIG. 4 shows another alternative embodiment of means for stopping the motion of the piston.

In accordance with the invention the syringe depicted has means 14 for limiting the inward motion of the piston so that end piece 15 does not come into contact with the inner end 20 of the cylindrical body 10. As shown in FIGS. 1 and 2 that means comprises an annular ring, which is preferably frictionally or otherwise attached to the outer end of piston 12 adjacent to thumb support area 13. The limiting means, however, can take other shapes òr forms, such as one or a plurality of limiting bars or protrusions 22 circumferentially spaced around the outside of the piston adjacent the thumb support area, as shown in FIG. 3. The limiting means may be separate means which are attached to the outside of the piston, or may be molded or otherwise formed as part of the piston itself. Another embodiment is shown in FIG. 4, where the limiting means comprises cylindrical member 23, which has a thin cylindrical portion inserted into the syringe tube, and a thicker shoulder portion which extends around the open end of the tube and arrests the inward motion of the plunger. This embodiment has several advantages, in that it can be simply snapped in place in standard syringe tubes, and it can be made in such proportions that the thin cylindrical portion within the tube not only holds the element in place, it also tends to stop the outward motion of the plunger when the proper blood sample size has been reached.

The size of the limiting means is preferably fixed so that when the inward motion of the plunger is stopped the space between the inner end of compressible end piece 15 and the inner end of the cylindrical body 10 is such that the amount of anticoagulant solution contained in that space, and in the free space within tip 16, connector 18 and hypodermic needle 19, is the proper amount to be mixed with the blood sample desired. Preferably, this amount of anticoagulant solution is between about 0.01 and 1.0 milliliter for every 5 milliliters of blood sample desired (i.e. from about 0.002 to 0.2 milliliter per milliliter of blood sample), more preferably between about 0.25 and 0.5 milliliter for every 5 milliliter of blood sample desired (i.e. from about 0.05 to 0.1 milliliter per milliliter of blood sample).

Compressible end piece 15 is designed to minimize the amount of friction between it and the inner surface of the cylindrical syringe body 10, while at the same time insuring that no air or other material is allowed to seep by the edges of the piston and thus contaminate the sample. As shown, the compressible end piece bears two ridges 15' which engage the inner surface of the cylindrical body. The end piece may have as few as one or as many as desired of such ridges, provided that the aforementioned functions are served. In the preferred embodiment the compressible end piece 15 is made out of compressible material having a low coefficient of friction with the material which makes up the inside of the syringe body. Silicone rubbers are most preferred, but other elastomeric materials such as natural or synthetic rubber, such as neoprene rubber, and other compressible plastics, such as polyvinyl chlorides, urethanes, polyesters, etc. known in the art, are suitable. As indicated above, a frictional fitting for connector 18 is shown in FIGS. 1 and 2, but other fittings are well known and are suitable, possibly even more suitable in certain circumstances. The most commonly used fitting for such sampling syringes is the luer lock fitting, in which the connecting element 18 has tabs, usually two in number, annularly displaced around the edge of the connector which is to be connected to the syringe. These tabs fit into a generally cylindrical fitting located on tip 16, the inside surface of which is threaded. The needle in this case is attached to the syringe simply by inserting the tab end of connector 18 into the fitting and screwing it on tightly. The luer lock fitting is generally preferred, albeit more expensive.

As will be readily appreciated, the problems experienced with prior blood sampling syringes are largely eliminated by the present invention. Because of the limiting member, which prevents the compression of the compressible end piece of the piston against the inner end wall of the cylindrical syringe body, no air is taken into the hypodermic needle after the expulsion of the air and excess anticoagulating solution, since the end piece is not allowed to compress against the inner end of the cylindrical tube and thus create a suction when pressure is released from the end of the piston. Similarly, the limitation as to the distance of travel allows standard syringes to be made with highly uniform volumes remaining after full insertion of the piston, thus giving uniform and accurate amounts of anticoagulant solution to be mixed with the blood sample, from one syringe to another. The tolerances on that are not nearly as high as in the case of the glass syringes, and all parts can be cheaply mass produced out of inexpensive raw materials. There is no breakage problem and the system is sufficiently simple and inexpensive to make the entire syringe disposable after the sample is analyzed or transferred to other equipment. Thus where a comparative series of tests are being run on a patient, for example, each syringe may be disposed of as soon as the test sample is transferred from the syringe to the testing equipment and each syringe when fully depressed will contain the same amount of the anticoagulant material. This insures that the samples will not coagulate or deteriorate between the time that they are taken from the patient and analyzed, and that too much anticoagulant will not be present in the blood sample as analyzed.

While the present syringe is particularly suitable for taking arterial blood samples, its suitability for other functions will be readily appreciated in the art. The syringe of the present invention is disposable and sufficiently inexpensive that it can be made readily available throughout the whole hospital. In using it there is no blood sample loss on account of breakage of the glass syringe after it has been filled with the sample.

The above constitutes a disclosure of the preferred embodiments of the present invention, but it will be apparent and appreciated by those skilled in the art that many changes and modifications may be made therein without departing from the essential spirit of the invention, which is indicated in the following claims.

I claim:

1. A method of drawing a blood sample into a syringe having a barrel with a barrel floor, a needle, a plunger with a compressible plunger tip forming with the end of said barrel a chamber containing anti-coagulant and means to limit the minimum size of said chamber by movement of said plunger to its innermost limit, said method comprising expelling from said chamber air which is present and anticoagulant in excess of an amount sufficient to prevent coagulation in the blood sample to be taken but less than an amount which will adversely affect the test to be performed by moving said plunger into the syringe to said innermost limit, and thereafter inserting said needle into a blood vessel of a patient and allowing the blood pressure of the patient to force the blood sample into the chamber and thereby move said plunger outwardly, whereby the blood sample mixes with the anticoagulant left in said syringe.

2. A method for drawing a blood sample according to claim 1 wherein said method comprises leaving in said chamber an amount of anticoagulant from about 0.002 to 0.2 milliliter per milliliter of blood sample to be taken.

3. A method for drawing a blood sample according to claim 1 wherein said method comprises leaving in said chamber an amount of anticoagulant from about 0.05 to 0.1 milliliter per milliliter of blood sample to be taken.

4. A method for drawing a blood sample into a syringe having a barrel with a barrel floor, a needle, a plunger with a compressible plunger tip forming with the end of said barrel a chamber containing anticoagulant, means to limit the innermost movement of said plunger to provide a minimum size of said chamber and to prevent deformation of said tip by compression thereof against said floor, and means to limit the outward movement of said plunger at a position where the desired sample volume has been withdrawn, said method comprising expelling from said chamber air which is present and anticoagulant in excess of an amount sufficient to prevent coagulation in the blood sample to be taken but less than an amount which will adversely affect the test to be performed by moving said plunger into the syringe to said innermost limit, inserting said needle into a blood vessel of a patient and allowing the blood pressure of the patient to force the blood sample into the chamber and thereby move said plunger outwardly until said outward limit means stops further outward movement and determines the volume of said sample, whereby the blood sample mixes with the anticoagulant left in said syringe, and with drawing said syringe with said sample from said blood vessel.

5. A method for drawing a blood sample according to claim 4 wherein said method comprises leaving in said chamber an amount of anticoagulant from about 0.002 to 0.2 milliliter per milliliter of blood sample to be taken.

6. A method for drawing a blood sample according to claim 4 wherein said method comprises leaving in said chamber an amount of anticoagulant from about 0.05 to 0.1 milliliter per milliliter of blood sample to be taken.

* * * * *